(12) United States Patent
Zeller et al.

(10) Patent No.: US 11,584,703 B2
(45) Date of Patent: Feb. 21, 2023

(54) PHOTOCHLORINATION OF CHLOROFORM TO CARBON TETRACHLORIDE

(71) Applicant: Occidental Chemical Corporation, Dallas, TX (US)

(72) Inventors: Robert L. Zeller, Seabrook, TX (US); Darrell Hollis, Conway Springs, KS (US); Keith S. Kramer, Andover, KS (US); Brian Calderwood, Wichita, KS (US); Rodney L. Klausmeyer, Wichita, KS (US)

(73) Assignee: OCCIDENTAL CHEMICAL CORPORATION, Dallas, TX (US)

( * ) Notice: Subject to any disclaimer, the term of this patent is extended or adjusted under 35 U.S.C. 154(b) by 0 days.

(21) Appl. No.: 17/034,948

(22) Filed: Sep. 28, 2020

(65) Prior Publication Data

US 2021/0009491 A1    Jan. 14, 2021

Related U.S. Application Data

(63) Continuation of application No. 16/315,035, filed as application No. PCT/US2017/040426 on Jun. 30, 2017, now Pat. No. 10,787,405.

(60) Provisional application No. 62/358,340, filed on Jul. 5, 2016.

(51) Int. Cl.
*C07C 17/10* (2006.01)
*C07C 19/041* (2006.01)

(52) U.S. Cl.
CPC ............ *C07C 19/041* (2013.01); *C07C 17/10* (2013.01)

(58) Field of Classification Search
None
See application file for complete search history.

(56) References Cited

U.S. PATENT DOCUMENTS

| | | | |
|---|---|---|---|
| 1,129,165 A | 2/1915 | Buchner | |
| 2,492,417 A | 12/1949 | Frilette | |
| 2,688,592 A | 9/1954 | Skeeters et al. | |
| 2,945,796 A | 7/1960 | Erik | |
| 3,076,043 A | 1/1963 | Dehn | |
| 3,676,508 A | 7/1972 | Krekeler et al. | |

(Continued)

FOREIGN PATENT DOCUMENTS

| | | |
|---|---|---|
| JP | 1973021923 B | 2/1973 |
| WO | 2013096311 A1 | 6/2013 |

OTHER PUBLICATIONS

Chiltz, G. et al. "Photochlorination of Chloroform" Nature, 180, 4594, pp. 1068-1069 (1957) (Year: 1957).*

(Continued)

*Primary Examiner* — Medhanit W Bahta
(74) *Attorney, Agent, or Firm* — Renner, Kenner; Arthur M. Reginelli

(57) ABSTRACT

A method of producing carbon tetrachloride, the method comprising the step of reacting chlorine with chloroform in the presence of electromagnetic radiation within a reaction mixture that includes the chlorine, the chloroform, and carbon tetrachloride, where the concentration of chloroform is less than 5000 ppm by weight relative to the weight of the reaction mixture, where the reaction mixture includes at least stoichiometric levels of chlorine relative to chloroform, where the electromagnetic radiation creates chloride radicals, and where the reaction mixture is well mixed.

19 Claims, 3 Drawing Sheets

(56) References Cited

U.S. PATENT DOCUMENTS

| | | | |
|---|---|---|---|
| 3,954,410 A | 5/1976 | Pohl et al. |
| 4,101,573 A | 7/1978 | Gehrmann et al. |
| 4,661,648 A | 4/1987 | Franklin |
| 8,258,353 B2 | 9/2012 | Kruper, Jr. et al. |
| 8,581,011 B2 | 11/2013 | Tirtowidjojo et al. |
| 8,907,149 B2 | 12/2014 | Tirtowidjojo et al. |
| 8,927,792 B2 | 1/2015 | Tirtowidjojo et al. |
| 9,067,855 B2 | 6/2015 | Grandbois et al. |
| 9,169,177 B2 | 10/2015 | Tirtowidjojo et al. |
| 9,199,899 B2 | 12/2015 | Grandbois et al. |
| 9,233,896 B2 | 1/2016 | Tirtowidjojo et al. |
| 9,284,239 B2 | 3/2016 | Grandbois et al. |

OTHER PUBLICATIONS

International Publication dated Sep. 26, 2017 for corresponding PCT/US2017/040426.
Office Action in Japanese Patent Application No. 2018-569011; dated Jan. 29, 2021.

* cited by examiner

PHOTOCHLORINATION OF CHLOROFORM TO CARBON TETRACHLORIDE

This application is a continuation application of U.S. Non-Provisional application Ser. No. 16/315,035 filed on Jan. 3, 2019, which is a National-Stage Application of International PCT/US2017/040426 filed on Jun. 30, 2017, which claims the benefit of U.S. Provisional Application Ser. No. 62/358,340 filed on Jul. 5, 2016, which are incorporated herein by reference.

FIELD OF THE INVENTION

Embodiments of the present invention are directed toward chlorination processes that include the photochlorination of chloroform to carbon tetrachloride.

BACKGROUND OF THE INVENTION

Carbon tetrachloride is a valuable feed stock for the synthesis of many important commercial chemicals. In particular, carbon tetrachloride often serves as a fundamental feed stock for the production of chlorinated propanes, which are used to produce hydrofluoroolefins (HFOs).

While originally formed by reacting chloroform with chlorine, most commercial processes synthesize carbon tetrachloride by chlorinating methane. Industrial methods for the chlorination of partially chlorinated methanes, such as methyl chloride, methylene chloride, and chloroform to carbon tetrachloride have also been proposed. For example, U.S. Pat. No. 9,169,177 discloses processes for the production of carbon tetrachloride from partially chlorinated methanes. In order to achieve greater reaction selectivity to carbon tetrachloride, this patent proposes maintaining conversion rates at less than 90%, which produces a product stream including chloroform and carbon tetrachloride with very little production of methyl chloride or methylene chloride. Those chlorinated methanes within the product stream that are not fully chlorinated (e.g. chloroform) are recycled back to the reactor for further chlorination.

In view of the increasing demand for carbon tetrachloride, industrial processes for the efficient synthesis of carbon tetrachloride are desirable.

SUMMARY OF THE INVENTION

One or more embodiments of the present invention provide a method of producing carbon tetrachloride, the method comprising the step of reacting chlorine with chloroform in the presence of electromagnetic radiation within a reaction mixture that includes the chlorine, the chloroform, and carbon tetrachloride, where the concentration of chloroform is less than 5000 ppm by weight relative to the weight of the reaction mixture, where the reaction mixture includes at least stoichiometric levels of chlorine relative to chloroform, where the electromagnetic radiation creates chloride radicals, and where the reaction mixture is well mixed.

Other embodiments of the present invention provide a process for producing carbon tetrachloride, the method comprising the step of (i) providing a reaction mixture within a reactor, where the reaction mixture includes carbon tetrachloride, chlorine, and chloroform; (ii) subjecting the reaction mixture to electromagnetic energy to thereby convert at least a portion of the chloroform to carbon tetrachloride; (iii) removing a product stream from the reactor, where said product stream includes carbon tetrachloride; and (iv) returning at least a portion of the product stream back to the reactor after said step of removing a product stream.

Still other embodiments of the present invention relate to an improvement in a process of the type where chloroform is converted to carbon tetrachloride by a photochlorination reaction where chlorine is subjected to ultraviolet light in the presence of the chloroform, the improvement comprising conducting the photochlorination reaction in a carbon tetrachloride medium that includes less than 5000 ppm chloroform and at least stoichiometric levels of chlorine within a well-mixed reactor including a reaction zone that is subjected to electromagnetic radiation having a wavelength of from about 200 to about 500 nm.

DETAILED DESCRIPTION OF ILLUSTRATIVE EMBODIMENTS

Embodiments of the invention are based, at least in part, on the discovery of a process for the production of carbon tetrachloride by photochlorination of chloroform. According to embodiments of the invention, the reaction takes place in a carbon tetrachloride medium that includes relatively high levels of chlorine and relatively low levels of chloroform. By practicing the methods of this invention, it has unexpectedly been found that industrially useful conversion levels can be achieved with substantial selectivity for carbon tetrachloride. Advantageously, it has been discovered that the formation of hexachloroethane, which results from the dimerization of two trichloromethyl radicals, can be maintained below commercially acceptable levels. As a result, the carbon tetrachloride product produced according to embodiments of the invention can be directly employed, as a crude product stream, in subsequent synthetic processes, such as the Kharasch reactions, without the need for costly purification to remove undesired heavy chlorinated organics.

Process Overview

Figure 1:
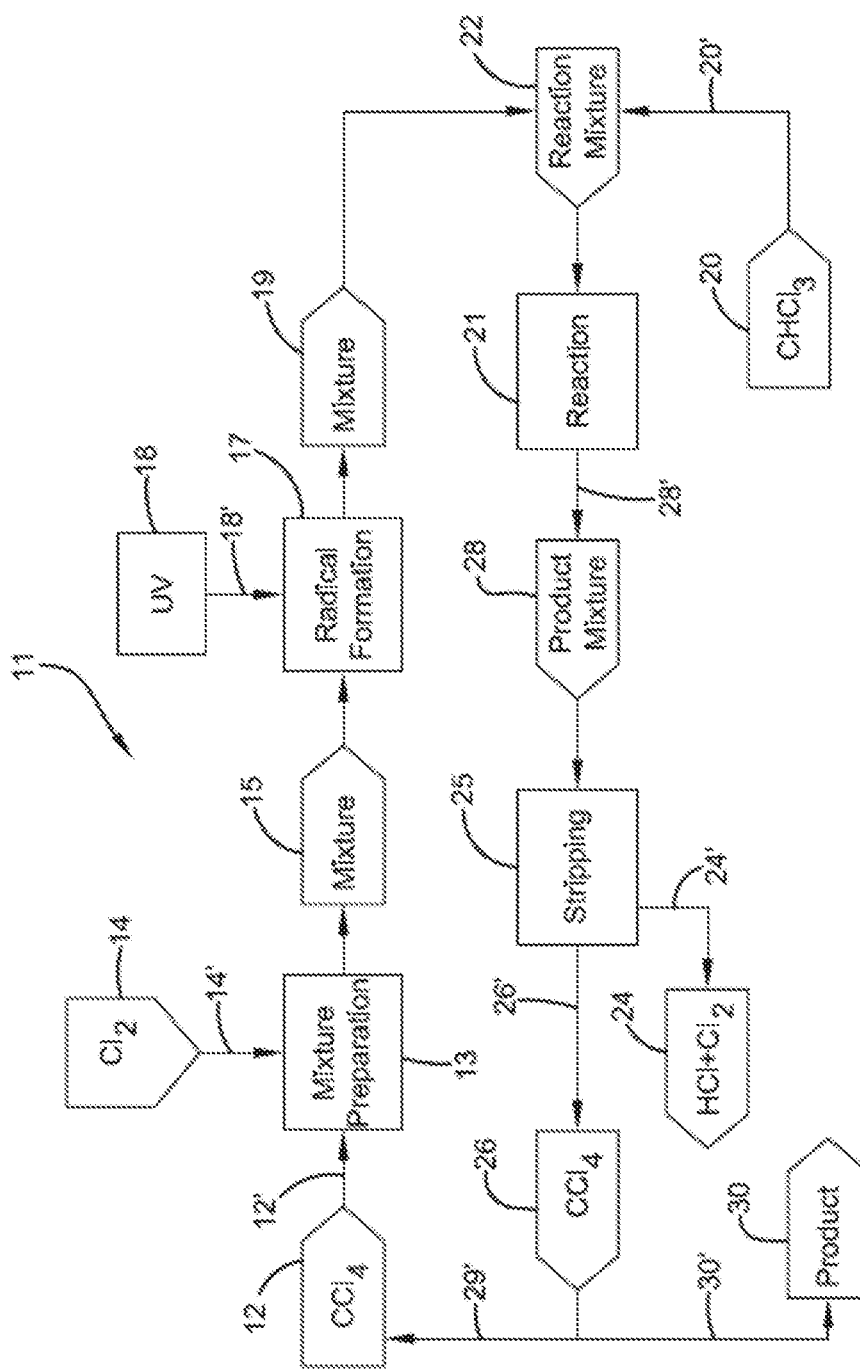
FIG. 1 is a flow chart representation of a process according to one or more embodiments of the present invention.

An overview of one or more embodiments of the present invention can be described with reference to FIG. 1, which shows a chlorination method 11. A carbon tetrachloride feed stream 12' and a chlorine gas feed stream 14' provide carbon tetrachloride 12 and chlorine gas 14 to introduction step 13 where carbon tetrachloride 12 and chlorine gas 14 are combined to thereby form a mixture 15 of carbon tetrachloride 12 and chlorine gas 14, which may also be referred to as initial mixture 15. Initial mixture 15 of carbon tetrachloride and chlorine gas is then subjected to electromagnetic radiation 18' from an electromagnetic radiation source 18 in a free radical forming step 17. Free radical forming step 17 forms a mixture 19 of chlorine gas, carbon tetrachloride, and chlorine free radicals, which may also be referred to as free radical mixture 19.

A chloroform feed stream 20' introduces chloroform 20 to free radical mixture 19 to form reaction mixture 22, and a reaction step 21 takes place that converts chloroform 20 to carbon tetrachloride, which is the desired product, and produces hydrochloric acid 24, which is a reaction byproduct. Carbon tetrachloride, chlorine, and hydrochloric acid are contained within product mixture 28 that may be identified as an intermediate product stream 28', or crude product stream 28', from reaction step 21. Crude product stream 28' may then be subjected to one or more additional processing steps 25, such as a stripping step 25, which may include, for example, gas stripping, which concentrates the carbon tetrachloride 26, via purified stream 26', by removing at least a portion of the chlorine and hydrochloric acid 24, via gas stream 24'.

In one or more embodiments, at least a portion of the purified carbon tetrachloride 26 may be recycled back to reaction step 21 via recycle stream 29'. At least a portion of purified carbon tetrachloride 26 may otherwise be recovered as product 30 via purified product stream 30'. As indicated above, purified stream 26' may advantageously be directly used as a reactant stream in subsequent chemical synthesis without the need for distillation processes that may otherwise be required to remove organic species such as heavy chlorinated organic compounds that are often a byproduct in the manufacture of chlorinated organics. With that said, it may nonetheless be desirable to further purify the product stream for particular uses. Accordingly, certain embodiments of this invention may include distillation processes to further purify stream 26'.

Figure 2:
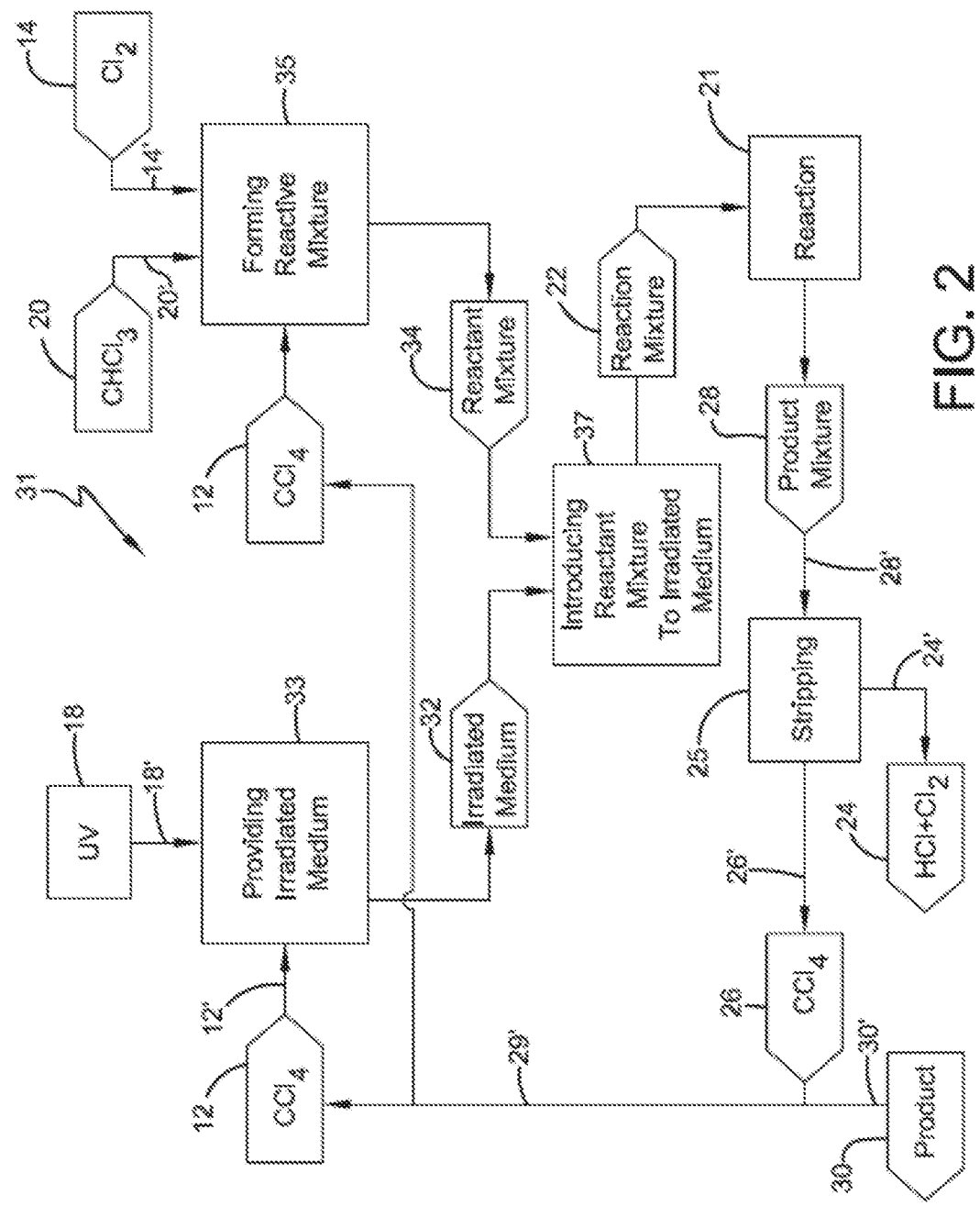
FIG. 2 is a flow chart representation of a process according to one or more embodiments of the present invention.

An alternate process scheme can be described with reference to FIG. 2, which shows chlorination method 31. Carbon tetrachloride 12 from feed stream 12' is combined with electromagnetic radiation 18' from radiation source 18 to provide an irradiated medium 32 within introducing step 33. Chloroform 20 from feed stream 20' is combined with chlorine 14 from feed stream 14' to form reactant mixture 34 within combining step 35. Carbon tetrachloride may optionally be combined with chloroform 20 and chlorine 14 within this step.

Irradiated medium 32 (which is continually subjected to the electromagnetic radiation) and reactant mixture 34 are introduced in step 37 to form reaction mixture 22 to give rise to reaction step 21, which converts chloroform 20 to carbon tetrachloride (i.e. the chloroform is chlorinated) and produces hydrochloric acid as a reaction byproduct. Carbon tetrachloride and hydrochloric acid are contained within product mixture 28 that may be identified as an intermediate product stream 28', or crude product stream 28', from reaction step 21. Crude product stream 28' may then be subjected to one or more additional processing steps 25, such as a stripping step 25, which may include, for example, a gas stripping, which concentrates the carbon tetrachloride 26, via purified stream 26', by removing at least a portion of the chlorine and hydrochloric acid 24, via gas stream 24'.

In one or more embodiments, at least a portion of the carbon tetrachloride 26 may be recycled back to initial step 33 and/or step 35 via recycle stream 29'. At least a portion of purified carbon tetrachloride 26 may otherwise be recovered as product 30 via purified product stream 30'. As indicated above with respect to FIG. 1, additional purifications, such as distillations, may be avoided. Yet, in certain embodiments, further purifications including distillations may be desired.

System for Performing Chlorination of Chloroform

A system for performing the methods of the invention can be described with reference to FIG. 3, which shows a system 51 for performing a chlorination method. System 51 includes reaction vessel 53, which includes inlet 57, vent 61, lamp 63, agitation element 65, and product outlet 67.

According to exemplary embodiments, chloroform 54 via chloroform feed stream 54' is combined with carbon tetrachloride via, for example, recycle stream 75' to form a reactant pre-mixture. Chlorine 52, via feed stream 52', is then combined (via, for example, an in-line sparger) with the reactant pre-mixture, which contains chloroform and carbon tetrachloride, to form a reactant mixture within stream 77'. As shown in FIG. 3, the chloroform and carbon tetrachloride can be mixed or otherwise agitated within a mixing device, such as an in-line mixer 55, prior to introduction of the chlorine. In other embodiments, which are not shown, the mixture including the chlorine, chloroform, and carbon tetrachloride, which is contained in stream 77', can likewise be agitated prior to introduction into reactor 53.

Feed stream 77 is then introduced to reactor 53 via inlet 57. As explained above, electromagnetic radiation from lamp 63 causes a chlorination reaction whereby chloroform is converted to carbon tetrachloride. The resultant carbon tetrachloride product is removed from reactor 53 via outlet 67 as product stream 66', which may also be referred to as crude product stream 66'. Product stream 66' may also include one or more of chloroform, chlorine, and hydrogen chloride, as well as other by-products at relatively low levels. Gaseous byproducts, such as hydrogen chloride and chlorine, can be removed from reactor 53 via vent 61 to form stream 79'. This stream may be neutralized for disposal or further separated to isolate chlorine and hydrochloric acid, which may then be used in other synthetic chemical processes.

Crude product stream 66' can be routed to tank 69, which may include a degassing tank, where crude product stream 66' can be concentrated by removal of light constituents such as chlorine and hydrogen chloride via gas stream 69', which can be combined with stream 79'. Through, for example, pump 71, crude product stream 66', which includes concentrated carbon tetrachloride, can be routed through recirculation loop 71', back to reactor 53 via carbon tetrachloride feed stream 75'. Alternatively, the concentrated crude product stream can be routed out of the system for storage and further use via carbon tetrachloride product stream 73'. In one or more embodiments, carbon tetrachloride product stream 73' can be subjected to additional electromagnetic radiation (as described herein relative to lamp 63), supplied from, for example, a polishing UV reactor or the like, to thereby photochlorinate any residual chloroform within the product stream. In one or more embodiments, additional chlorine can be added to the product stream treated in this downstream polishing reactor.

It should be appreciated that according to certain embodiments of the invention, recirculation loop 71' is optional inasmuch as crude product stream 66' can be directly routed to other processes (i.e. stream 66' can be directly routed to 73'). In these embodiments, however, alternate sources of carbon tetrachloride must be used for the reaction medium.

It should therefore be appreciated that the process (and system) of the present invention can be operated as a continuous process wherein reactants are continuously fed to a reactor and product is continuously removed from the reactor. Moreover, the process requirements for carbon tetrachloride can be satisfied from the product stream deriving from the system (e.g. carbon tetrachloride product stream 66' can be recycled back to reactor 53 via input stream 75'). In one or more embodiments, following initial start-up of the system, where external sources of carbon tetrachloride are required (e.g. carbon tetrachloride 12), the process of the invention can receive greater than 90%, in other embodiments greater than 95%, and in other embodiments greater than 99% of the carbon tetrachloride requirements for the operation of the system from carbon tetrachloride recycled from the system (e.g. recycled through loop 71').

It should also be appreciated that various modifications can be made to system 51 without departing from the present invention. For example, chlorine 52 and chloroform 54 can be directly injected into reactor 53 via respective feed streams without the need to premix chlorine 52 and chloroform 54 prior to introduction into reaction vessel 53. In particular embodiments, chloroform feed stream 54' can be introduced below the liquid level within the reactor (e.g. via a dip tube). In these or other embodiments, chlorine feed stream 52' can likewise be introduced below the liquid level via, for example, a sparger. In one or more embodiments, the separate and distinct feed streams can be first combined with carbon tetrachloride and then directly introduced into reactor 53. Also, reactor 53 can be configured to provide for flow of material from the bottom to the top of the reactor, as generally shown in FIG. 3, or the flow of the material can be reversed such that inputs are received at the top of the reactor and the product is removed from the bottom of the reactor.

In one or more embodiments, inlet 57 may include a dispersing device such as a sparger or dip tube, and vessel 53 may include multiple inlets (not shown).

Figure 3:
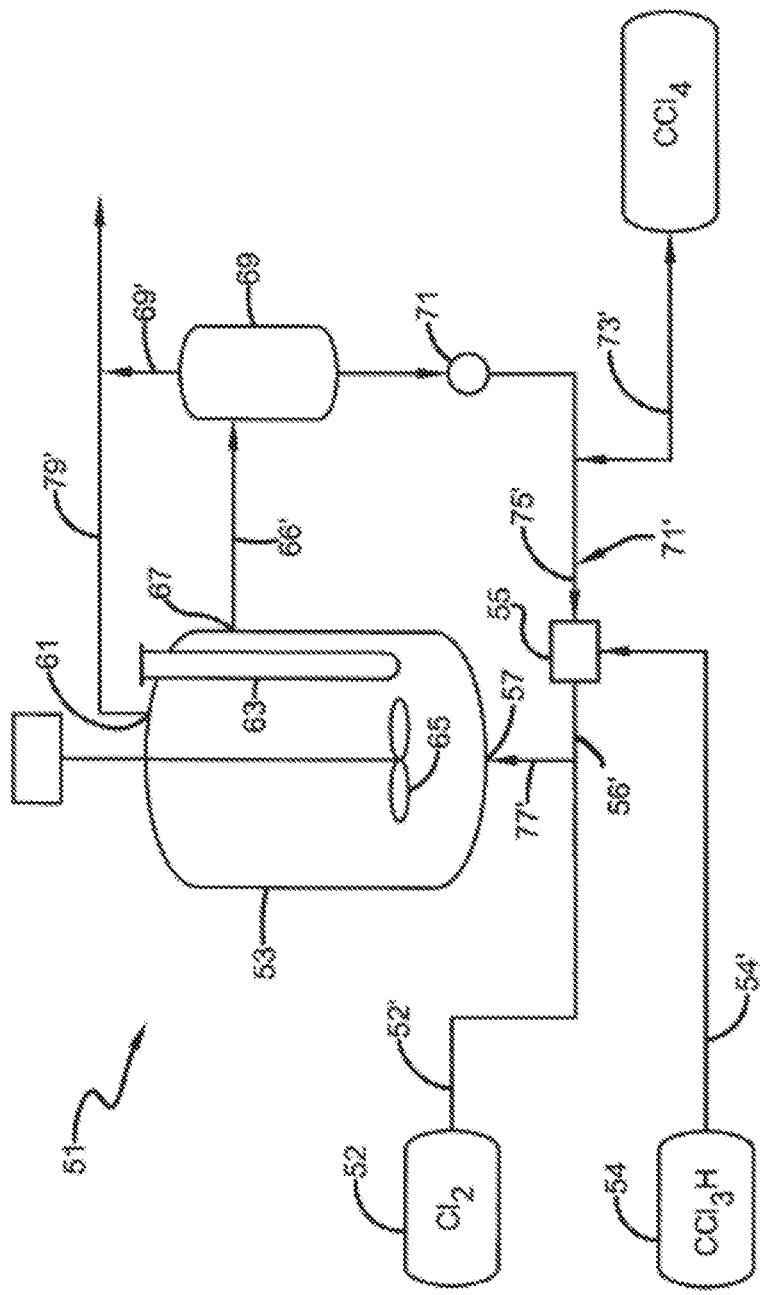
FIG. 3 is a schematic representation of a system for conducting a process according to embodiments of the present invention.

In one or more embodiments, vessel 53 may include a single lamp, as shown in FIG. 3, or it may include multiple lamps. In one or more embodiments, lamp 63 may include ultraviolet lamps, lasers, and light-emitting diodes. In particular embodiments, the lamps include mercury vapor arc lamps such as Hanovia lamps. In one or more embodiments, the lamp(s) (e.g. lamp 63) may be partially immersed within the reaction medium contained within vessel 53 or they may be fully immersed in the reaction medium. In other embodiments, not shown, the lamps, may be external to the interior of the reactor but nonetheless situated to emit the desired electromagnetic radiation into the reactor medium.

Also, reaction vessel 53 may be equipped with a temperature regulating system such as a heating/cooling jacket. In one or more embodiments, agitation element 65 may include a single mechanical agitator, such as shown in FIG. 3, or multiple agitation devices may be employed. As is known in the art, various mixing configurations can be used including top and bottom mounted mixers.

In one or more embodiments, reactor 58 is configured to include a dark zone, which is an area within the reactor that is not subjected to appreciable levels of electromagnetic radiation that gives rise to the desired photochlorination reaction described herein. The dark zone advantageously provides time and space for the input stream 77' to become diluted and well mixed within the greater volume of carbon tetrachloride contained within reactor 53 prior to the chlorine becoming radicalized and/or the chlorine radicals reacting with the chloroform in the presence of appropriate electromagnetic radiation. As the skilled person will appreciate, the dark zone can be created by employing several mechanisms. For example, a physical obstruction can be placed within the reactor to thereby shield an area from the electromagnetic radiation emitted from lamp 63. Alternatively, or in combination with a physical obstruction, a dark zone can be formed by providing adequate distance between lamp 63 and the desired location of the dark zone. As a skilled person will appreciate, inlet 57 is desirably located within or adjacent to the dark zone.

It should be appreciated that at start up, reactor 53 is initially charged with carbon tetrachloride to form an initial medium in which the reaction takes place. In one or more embodiments, the reactor is devoid or substantially devoid of chloroform at the beginning of the reaction so as to avoid having excess chloroform relative to chlorine at any point in the reaction. Once the reaction is underway, the appropriate balance of chlorine and chloroform, and hence carbon tetrachloride as well, within reactor 53, which balance will be described herein below, can be maintained by regulating the chlorine, chloroform, and optionally carbon tetrachloride inputs into reactor 53.

While this system has been described with reference to specific embodiments of the invention, the skilled person can adapt the system, without undue calculation or experimentation, to accommodate other processes described herein.

Characteristics of Carbon Tetrachloride Feed Stream

In one or more embodiments, carbon tetrachloride feed stream (e.g. 12', 75') is substantially carbon tetrachloride, which refers to a feed stream that does not include appreciable amounts of constituents other than carbon tetrachloride. In one or more embodiments, carbon tetrachloride feed stream (e.g. 12', 75') consists essentially of carbon tetrachloride, which refers to a composition that is free of other constituents that would otherwise materially impact the basic and novel characteristics of embodiments of the invention. In one or more embodiments, carbon tetrachloride feed stream (e.g. 12', 75') consists of carbon tetrachloride. In one or more embodiments, the carbon tetrachloride is technical-grade carbon tetrachloride. In one or more embodiments, carbon tetrachloride feed stream 12', 75' includes from about 99.9 to about 100 wt %, carbon tetrachloride. In one or more embodiments, carbon tetrachloride feed stream (e.g. 12', 75') includes less than 7000 ppm, in other embodiments less than 6000 ppm, in other embodiments less than 5500 ppm, in other embodiments 5000 ppm, in other embodiments less than 2500 ppm, in other embodiments less than 1000 ppm, in other embodiments less than 750 ppm, in other embodiments less than 500 ppm, and in other embodiments less than 100 ppm of chlorinated organic constituents other than carbon tetrachloride.

Characteristics of Chlorine Feed Stream

In one or more embodiments, chlorine feed stream (e.g. 14', 52') is substantially chlorine, which refers to a feed stream that does not include appreciable amounts of constituents other than chlorine gas. In one or more embodiments, chlorine gas feed stream (e.g. 14', 52') consists essentially of chlorine gas, which refers to a composition that is free of other constituents that would otherwise materially impact the basic and novel characteristics of embodiments of the invention. In one or more embodiments, chlorine gas feed stream (e.g. 14', 52') consists of chlorine gas. In one or more embodiments, chlorine feed stream (e.g. 14', 52') includes from about 99.5 to about 100 vol %, chlorine. In one or more embodiments, chlorine feed stream (e.g. 14', 54') includes less than 5000 ppm, in other embodiments less than 1000 ppm, in other embodiments less than 750 ppm, and in other embodiments less than 500 ppm of constituents other than chlorine.

In one or more embodiments, chlorine gas feed stream (e.g. 14', 52') is sparged with nitrogen or other inert media, such as argon, prior to introduction to the system. Accordingly, in one or more embodiments, chlorine gas feed stream (e.g. 14', 52') is substantially devoid of oxygen, which refers to a feed stream that does not include appreciable amounts of oxygen. In one or more embodiments, chlorine feed stream (e.g. 14', 52') includes less than 2500 ppm, in other embodiments less than 1000 ppm, in other embodiments less than 750 ppm, in other embodiments less than 500 ppm, and in other embodiments less than 250 ppm of oxygen.

Characteristics of Chloroform Feed

In one or more embodiments, chloroform feed stream 20', 54' is substantially chloroform, which refers to a feed stream that does not include appreciable amounts of constituents other than chloroform. In one or more embodiments, chloroform feed stream 20', 54' consists essentially of chloroform, which refers to a composition that is free of other constituents that would otherwise materially impact the basic and novel characteristics of embodiments of the invention. In one or more embodiments, chloroform feed stream 20', 62 consists of chloroform. In one or more embodiments, the chloroform is technical-grade chloroform. In other embodiments, fluorocarbon-grade chloroform is employed. In yet other embodiments, the chloroform may include a feed from other synthetic processes such as the production of chloromethanes. In one or more embodiments, chloroform feed stream 20', 54' includes from about 99.8 to about 100 wt %, chloroform. In one or more embodiments, chloroform feed stream 20', 62 includes less than 5000 ppm, in other embodiments less than 2500 ppm, in other embodiments less than 2000 ppm, in other embodiments less than 1000 ppm, in other embodiments less than 750 ppm, and in other embodiments less than 500 ppm of constituents other than chloroform.

Characteristics of Reaction Mixture

In one or more embodiments, the reaction mixture (e.g. reaction mixture 22 or the contents of reactor 53), which includes carbon tetrachloride, chlorine, hydrogen chloride, and chloroform, as well as residual byproducts such as heavy chlorinated organics, is maintained at a temperature and pressure that will maintain the carbon tetrachloride in the liquid state. As the skilled person will appreciate, a higher operating pressure will allow for a higher operating temperature since the processes of the invention are desirably conducted in the liquid phase.

In one or more embodiments, the reaction mixture (e.g. mixture 22 or the contents of reactor 53), during and optionally prior to the reaction or chlorination step (e.g. reaction step 21), is maintained at a temperature greater than 10° C., in other embodiments greater than 15° C., and in other embodiments greater than 20° C. In these or other embodiments, the reaction mixture is maintained, both prior to or during the reaction step, at a temperature less than 70° C., in other embodiments less than 60° C., and in other embodiments less than 50° C. In one or more embodiments, the reaction mixture is maintained, both prior to or during reaction step, at a temperature of from about 10 to about 70° C., in other embodiments from about 15 to about 60° C., or in other embodiments from about 20 to about 50° C. In one or more embodiments, the reaction mixture (e.g. mixture 22 or the contents of reactor 53) is maintained at a temperature and pressure sufficient to maintain relatively high levels of chlorine, as well as the chloroform, within the carbon tetrachloride medium.

In one or more embodiments, reaction mixture (e.g. mixture 22 or the contents of reactor 53) is maintained, both prior to or during the reaction or chlorination step (e.g. step 21), under a pressure greater than 0.8, in other embodiments greater than 0.9, and in other embodiments greater than 0.95 atmospheres. In these or other embodiments, reaction mixture is maintained, both prior to or during the reaction step, under a pressure less than 15, in other embodiments less than 10, and in other embodiments less than 5 atmospheres. In one or more embodiments, the reaction mixture is maintained, both prior to or during the reaction step, under a pressure from about 0.8 to about 15, in other embodiments from about 0.9 to about 10, or in other embodiments from about 0.95 to about 5 atmospheres.

In one or more embodiments, the reaction mixture (e.g. mixture 22 or the contents of reactor 53) is maintained, both prior to or during the reaction or chlorination step (e.g. step 21), under agitation. In one or more embodiments, the agitation is sufficient to achieve turbulent flow through the reactor in which the reaction takes place (e.g. reactor 53). In one or more embodiments, the agitation is sufficient to achieve turbulence that can be quantified by a Reynolds number of greater than 4000, in other embodiments greater than 10,000, and in other embodiments greater than 20,000. In these or other embodiments, the reaction mixture is maintained, both prior to or during the reaction step (e.g. step 21), is agitated to provide turbulence that can be quantified by a Reynolds number of from about 4000 to about 30,000, in other embodiments from about 8,000 to about 28,000, or in other embodiments from about 10,000 to about 26,000. In one or more embodiments, the photochlorination process of the present invention is conducted within a reactor (e.g. reactor 53) that is a well-mixed reactor with sufficient agitation to approach the ideal continuously-stirred tank reactor (CSTR).

As suggested above, the introduction of chloroform to the reaction mixture (e.g. mixture 22 or the contents of reactor 53), which feed rate thereby regulates the concentration of chloroform within the reactor, is provided in an amount and in a manner that gives substantially instantaneous reaction of the chloroform to carbon tetrachloride in the presence of the UV light. It has been unexpectedly discovered that the dilution and dispersion of the chloroform, which is miscible in the carbon tetrachloride, immediately prior to and during the reaction step (e.g. step 21) is a critical parameter to obtaining the advantageous results of the invention.

In one or more embodiments, the feed rate of the chloroform to the reactor (e.g. reactor 53) can be quantified relative to the carbon tetrachloride within the reactor. In one or more embodiments, the feed rate of chloroform is greater than 10, in other embodiments greater than 15, in other embodiments greater than 25, in other embodiments greater than 35, in other embodiments greater than 45, in other embodiments greater than 55, in other embodiments greater than 65, in other embodiments greater than 75, in other embodiments greater than 85, in other embodiments greater than 95, in other embodiments greater than 110, and in other embodiments greater than 120 pounds per hour per 1000 pounds of carbon tetrachloride within the reactor. In these or other embodiments, the feed rate of chloroform is less than 1000, in other embodiments less than 800, in other embodiments less than 650, in other embodiments less than 500, in other embodiments less than 250, in other embodiments less than 200, in other embodiments less than 150, in other embodiments less than 125, in other embodiments less than 100, in other embodiments less than 80, in other embodiments less than 60, in other embodiments less than 40, in other embodiments less than 30, and in other embodiments less than 25 pounds per hour per 1000 pounds of carbon tetrachloride within the reactor. In one or more embodiments, the feed rate of the chloroform is from about 10 to about 1000, in other embodiments from about 25 from about 650, and in other embodiments from about 55 to about 200 pounds per hour per 1000 pounds of carbon tetrachloride within the reactor.

In one or more embodiments, the dilution of the chloroform can also be quantified based upon the amount of chloroform within the reaction mixture (e.g. mixture 22 or the contents of reactor 53). For example, the concentration of chloroform within the reaction mixture can be quantified based upon the weight of chloroform relative to the weight of the reaction mixture, which includes the carbon tetrachloride, chlorine, hydrogen chloride, and chloroform within the reaction mixture. As a skilled person will appreciate, these amounts (i.e. the chloroform within the reaction mixture) can be determined by measuring the amount of chloroform within the reactor effluent (i.e. at the outlet), which in a well-stirred reactor is equivalent to the amount of chloroform at the reaction zone, where the reaction zone refers to that location within the reaction medium (i.e. within the reactor) in which chlorination of the chloroform takes place (i.e. the reaction mixture is subjected to the appropriate wavelength of electromagnetic radiation). In one or more embodiments, the concentration of chloroform within the reaction mixture is less than 5,000 ppm (by weight), in other embodiments less than 4,000 ppm, in other embodiments less than 3,000 ppm, and in other embodiments less than 2,000 ppm chloroform based upon the total weight of the reaction mixture. In one or more embodiments, the concentration of chloroform within the reaction mixture is from about 1 to about 5,000 ppm, in other embodiments from about 50 to about 3,000 ppm, and in other embodiments from about 100 to about 2,000 ppm chloroform based upon the entire weight of the reaction mixture.

As suggested above, the amount of chlorine present during the reaction step (e.g. reaction step 21) or, stated another way, within the reaction mixture, is believed to be an important parameter for practicing the invention. In one or more embodiments, the introduction of chlorine to the reaction mixture (e.g. to vessel 53) is provided in an amount and in a manner that provides the reaction with at least a stoichiometric amount, or a stoichiometric excess of, chlorine, relative to the chloroform. In one or more embodiments, the concentration of the chlorine within the reaction medium (i.e. carbon tetrachloride) is at the saturation level for chlorine within the carbon tetrachloride at the temperature and pressure at which the reaction is performed. In one or more embodiments, the amount of chlorine with the reactor (e.g. reactor 53) is sufficient to maintain appreciable levels of chlorine within the head space of the reactor. To the extent that excess chlorine is fed to the reactor relative to the chloroform, the concentration of chlorine within the reactor can continue to build over time until a saturation level is achieved relative to the temperature and pressure within the reactor, although recirculation of the carbon tetrachloride through a recirculation loop may serve to modulate the amount if chlorine within the reactor.

In one or more embodiments, the amount of chlorine introduced to the reaction mixture can be quantified based upon the molar ratio of chlorine to chloroform fed to the reactor. In one or more embodiments, the molar ratio of chlorine to chloroform that is fed to, for example, reactor 53, is greater than 1.00:1.00, in other embodiments greater than 1.02:1.00, and in other embodiments greater than 1.04:1.00. In one or more embodiments, the molar ratio of chlorine to chloroform is from about 1.00:1.00 to about 1.10:1.00, in other embodiments from about 1.01:1.00 to about 1.08:1.00, and in other embodiments from about 1.02:1.00 to about 1.06:1.00.

In these or other embodiments, the amount of chlorine employed in the process of the present invention can be quantified based on the concentration of chlorine within the reaction mixture. As a skilled person will appreciate, these amounts (i.e. the chlorine within the reaction mixture) can be determined by measuring the amount of chlorine within the reactor effluent (i.e. at the outlet), which in a well-stirred reactor is equivalent to the amount of chlorine at the reaction zone, where the reaction zone refers to that location within the reaction medium (i.e. within the reactor) in which chlorination of the chloroform takes place. In one or more embodiments, the concentration of chlorine within the effluent is greater than 0.01 wt %, in other embodiments greater than 0.1 wt %, in other embodiments greater than 0.3 wt %, in other embodiments greater than 0.6 wt %, in other embodiments greater than 1.2 wt %, in other embodiments greater than 1.5 wt %, in other embodiments greater than 1.8 wt %, and in other embodiments greater than 2.0 wt % based upon the total weight of the reaction mixture. In these or other embodiments, the concentration of chlorine within the reactor effluent is at saturation level for the given temperature and pressure, in other embodiments less than 5 wt %, in other embodiments less than 4.6 wt %, and in other embodiments less than 4.2 wt % based upon the total weight of the reaction mixture. In one or more embodiments, the concentration of chlorine within the reactor effluent is from about 0.01 wt % to saturation, in other embodiments from about 0.1 to about 5 wt %, in other embodiments from about 0.3 to about 5 wt %, in other embodiments from about 1.8 to about 4.6 wt %, and in other embodiments from about 2.0 wt % to about 4.2 wt % based upon the total weight of the reaction mixture.

Characteristics of Electromagnetic Radiation

In one or more embodiments, the electromagnetic radiation employed in practicing the present invention (e.g. generated by lamp 63) is characterized by including a wave length of from about 200 to about 500 nm, in other embodiments from about 200 to about 400 nm, in other embodiment from about 280 to about 380 nm, and in other embodiments from about 300 to about 350. In these or other embodiments, the electromagnetic radiation is characterized by a wavelength distribution, based upon relative intensity, where from about 50 to about 60% of the intensity has a wave length of about 280 to about 435 nm, in these or other embodiments where from about 40 to about 50% of the intensity has a wave length of about 300 to about 380 nm, and in these or other embodiments where from about 20 to about 30% of the intensity has a wave length of about 330 to about 370 nm. In one or more embodiments, the electromagnetic radiation includes ultraviolet light.

In one or more embodiments, the electromagnetic radiation is provided from one or more light producing lamps that operate at 40 to about 20,000, in other embodiments from about 75 to about 18,000, an in other embodiments from about 100 to about 10,000 W. In one or more embodiments, the electromagnetic radiation is provided from one or more mercury lamps. In specific embodiments, the electromagnetic radiation is provided from a Hanovia Mercury Vapor Arc Lamp.

Characteristics of Product Stream

As discussed above, the carbon tetrachloride crude product stream (e.g. streams 28' and 66') includes the desired carbon tetrachloride product, chlorine, and hydrogen chloride as well as residual byproducts such as heavy chlorinated organics. In one or more embodiments, these product streams (e.g. 28', 66') are substantially carbon tetrachloride, chloroform, hydrogen chloride, and optionally chlorine, which refers to a product stream that does not include appreciable amounts of constituents other than carbon tetrachloride, chloroform, hydrogen chloride, and optionally chlorine. In one or more embodiments, the product stream (e.g. 28', 66') consists essentially of carbon tetrachloride, optionally chloroform, optionally hydrogen chloride, and optionally chlorine, which refers to a composition that is free of other constituents that would otherwise materially impact the basic and novel characteristics of embodiments of the invention. In one or more embodiments, the product stream (e.g. 28', 66') consists of carbon tetrachloride, optionally chloroform, optionally hydrogen chloride, and optionally chlorine.

In one or more embodiments, the product stream (e.g. 28', 66') includes less than 2500 ppm, in other embodiments less than 1000 ppm, in other embodiments less than 500, in other embodiments less than 250, and in other embodiments less than 100 ppm (parts per million by weight) chlorinated hydrocarbons other than carbon tetrachloride (e.g. hexachloroethane).

In one or more embodiments, the product stream (e.g. 28', 66') includes less than 2500 ppm, in other embodiments less than 1000 ppm, in other embodiments less than 750, and in other embodiments less than 500 ppm (parts per million by weight) of constituents other than carbon tetrachloride, hydrogen chloride, and chlorine.

In one or more embodiments, the product stream (e.g. 28', 66') is characterized by an advantageously low level of chloroform, which is indicative of high reaction yield. In one or more embodiments, the reaction yield, relative to chloroform, is greater than 90.00%, in other embodiments greater than 92.00%, in other embodiments greater than 95.00%, in other embodiments greater than 97.00%, in other embodiments greater than 98.00%, in other embodiments greater than 99.00%, in other embodiments greater than 99.50%, and in other embodiments greater than 99.99%. In particular embodiments, the yield, relative to chloroform, is 100%. As a result, product stream 28', 66' includes less than 6000 ppm, in other embodiments less than 5500 ppm, in other embodiments less than 5000 ppm, in other embodiments less than 4500 ppm, in other embodiments less than 4000 ppm, in other embodiments less than 3000 ppm, in other embodiments less than 2000 ppm, in other embodiments less than 1000 ppm, in other embodiments less than 500 ppm, in other embodiments less than 250, in other embodiments less than 100, in other embodiments less than 50, and in other embodiments less than 10 ppm (parts per million by weight) chloroform.

Reaction Mechanism

As suggested herein, the manner and sequence of this process is believed to encourage the formation chlorine free radicals and reaction of these radicals with chloroform prior to any side reactions (e.g. the dimerization of chloroform) to thereby increase the selectivity of the reaction. Without wishing to be bound by any particular theory, it is believed that the following reactions take place during one or more steps of the present invention:

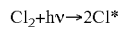  (1) Initiation

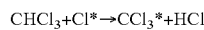  (2) Propagation

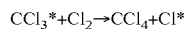  (3) Propagation

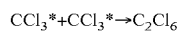  (4) Termination

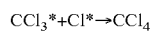  (5) Termination

  (6) Termination.

Reactions 1-3 are the desired pathway to convert chloroform and chlorine gas into carbon tetrachloride and HCl byproduct. Reaction 5 leads to the desired product, but at the cost of terminating the free radical reaction chain. Reaction 4 terminates the chain and includes the formation of hexachloroethane by the dimerization of two trichloromethyl radicals; this reaction is substantially avoided by the present invention. Reaction 6 terminates the reaction chain but provides chlorine that can again generate free radicals in the presence of an initiator, such as UV light.

INDUSTRIAL APPLICABILITY

In one or more embodiments, the crude product stream (e.g. streams 28' or 66', 73'), may be used in the synthesis of chlorinated organic compounds. As indicated above, the process of one or more embodiments of the present invention advantageously provides a product stream that can be directly used in these downstream synthetic processes without the need for separation steps, such as distillation steps, to remove heavier chlorinated organic byproducts such as hexachloroethane.

In one or more embodiments, the carbon tetrachloride produced according to embodiments of the invention, as a crude product stream, can be directly combined with an olefin, such as ethylene or vinyl chloride, and reacted in the presence of an appropriate catalyst to form a chlorinated propane and/or chlorinated propene. In this respect, U.S. Pat. Nos. 6,187,978, and 6,313,360, and U.S. Publication Nos. 2012/0310020, 2009/0216055, and 2004/0225166 are hereby incorporated by reference.

In order to demonstrate the practice of the present invention, the following examples have been prepared and tested. The examples should not, however, be viewed as limiting the scope of the invention. The claims will serve to define the invention.

EXAMPLES

Examples 1-5

All the reactions in Examples 1-5 were carried out in a jacketed one-liter Pyrex stirred reactor (Ace reactor #7864-12) with a jacketed, water-cooled quartz immersion lamp well (Ace #7874-38). A 450 watt medium pressure mercury vapor arc lamp (Ace #7825-35) provided the illumination. A magnetic stir bar was used to ensure the reactor was well mixed; it was calculated that mix conditions within the reactor would yield a Reynolds number of about 24,400. Each experiment was conducted over a time interval of about six hours. Examples were analyzed by gas chromatography using a 30 m×0.53 mm DB-624 column and a thermal conductivity detector (TCD). Selectivity was calculated by measuring the concentration of hexachloroethane (the only undesirable by product detected), calculating the percentage of the chloroform consumed in forming it, and subtracting that from 100%. Relevant data from each example is summarized in Table 1 below.

Example 1

The reactor was charged with 1158 grams of a mixture containing 4.4 wt % chloroform and 95.6 wt % carbon tetrachloride. The reaction temperature was maintained at 35° C. The UV lamp was turned on. After five minutes, 100 wt % chloroform was fed at a rate of 0.29 g/min and 100 wt % chlorine gas was sparged into the solution at a rate of 0.18 g/min for 6 hours. Chlorine was fed at 70% of what was required stoichiometrically for the reaction. Samples were taken hourly over a six hour time span. The selectivity of chloroform to carbon tetrachloride was determined to be 65.2%, with the balance of the chloroform producing hexachloroethane. The data collected hourly showed no changes beyond normal experimental variations in selectivity over time.

Example 2

The reactor was charged with 1196 grams of 100 wt % carbon tetrachloride. The reaction temperature was maintained at 35° C. The UV lamp was turned on. After four minutes, 100% chloroform was fed at a rate of 0.30 g/min and 100 wt % chlorine was sparged into the solution at a rate of 0.18 g/min for 6 hours, 10 minutes. Chlorine was fed at what was required stoichiometrically for the reaction. Samples were taken hourly. The selectivity of chloroform to carbon tetrachloride was determined to be approximately 100%, with chloroform conversion to hexachloroethane being less than 0.003% (non-detectable at a method detection limit). The data collected hourly showed no changes beyond normal experimental variations in selectivity over time.

Example 3

The reactor was charged with 1190 grams of 100 wt % carbon tetrachloride. The reaction temperature was maintained at 25° C. The UV lamp was turned on. After four minutes, 100 wt % chloroform was fed at a rate of 0.30 g/min and 100 wt % chlorine was sparged into the solution at a rate of 0.18 g/min for 5 hours. Chlorine was fed at what was required stoichiometrically for the reaction. Samples were taken hourly. The selectivity of chloroform to carbon tetrachloride was determined to be approximately 100%, with chloroform conversion to hexachloroethane being less than 0.003% (non-detectable at a method detection limit). The data collected hourly showed no changes beyond normal experimental variations in selectivity over time.

Example 4

The reactor was charged with 1207 grams of 100 wt % carbon tetrachloride. The reaction temperature was maintained at 35° C. Chlorine was sparged at a rate of 0.18 g/min. The UV lamp was turned on after 30 minutes. After five additional minutes, 100% chloroform was fed at a rate of 0.31 g/min. Chlorine was fed in excess of what was required stoichiometrically for the reaction. Samples were taken hourly. The selectivity of chloroform to carbon tetrachloride was determined to be approximately 100%, with chloroform conversion to hexachloroethane being less than 0.003% (non-detectable at a method detection limit). The data collected hourly showed no changes beyond normal experimental variations in selectivity over time.

Example 5

The reactor was charged with 1225 grams of a mixture containing approximately 5000 ppm by weight chloroform with the balance carbon tetrachloride. The reaction temperature was maintained at 35° C. The UV lamp was turned on. After five minutes, 100 wt % chloroform was fed at a rate of 0.30 g/min and 100 wt % chlorine gas was sparged into the solution at a rate of 0.18 g/min for 5 hours. Chlorine was fed at 94% of what was required stoichiometrically for the reaction. Samples were taken hourly. The selectivity of chloroform to carbon tetrachloride was determined to be 81.4%, with the balance of the chloroform producing hex-achloroethane. The data collected hourly showed no changes beyond normal experimental variations in selectivity over time.

TABLE 1

| Example | 1 | 2 | 3 | 4 | 5 |
|---|---|---|---|---|---|
| lb/hr CHCl$_3$/1000 lbs CCl$_4$ | 14.97 | 15.26 | 14.87 | 15.49 | 14.67 |
| Mole Ratio (Cl$_2$:CHCl$_3$) | 0.70 | 1.0 | 1.02 | 1.07 | 0.94 |
| Initial CHCl$_3$ in Reactor (wt %) | 4.4% | 0.0% | 0.0% | 0.0% | 0.5% |
| Temperature, ° C. | 35 | 35 | 25 | 35 | 35 |
| Borosilicate Glass Filter on Lamp | No | No | No | No | No |
| CHCl$_3$ Conversion | 88.9% | 100.0% | 99.9% | 100.0% | 93.8% |
| Selectivity to CCl$_4$ | 65.2% | 100.0% | 100.0% | 100.0% | 81.4% |

The data in Table 1 shows that Examples 1 and 5 fall outside practice of the present invention since the conversion rate and selectivity of the reaction to carbon tetrachloride were below acceptable levels. The product stream resulting from both Examples 1 and 5 would require further distillation of the product stream to remove the hexachloroethane. Examples 2, 3 and 4 provide highly advantageous results, which suggests that the excess chloroform present during Examples 1 and 5 negatively impact the reaction.

Examples 6-9

For Examples 6-9, the reactor system used in Examples 1-5 was modified to provide a circulation loop arranged so that chloroform could be combined with carbon tetrachloride outside the reactor, and then chlorine could be sparged into this mixture prior to introducing the blend of chloroform, carbon tetrachloride and chlorine into the reactor. A magnetic stir bar was used to ensure the reactor was well mixed; it was calculated that mix conditions within the reactor would yield a Reynolds number of about 20,000. Each experiment was conducted over a time interval of about 90 minutes. Product was drawn off of the top of the reactor into a product receiver to maintain a constant volume of liquid in the reactor throughout each experiment. A 100 watt medium pressure mercury vapor lamp (Ace #7825-30) was employed that was fitted with a borosilicate glass filter (Ace #7835 44) to attenuate the radiation at lower wavelengths. Relevant data from each example is summarized in Table 2 below.

Example 6

The reactor was charged with 957 grams of carbon tetrachloride. The reaction temperature was maintained at 35° C. The UV lamp was turned on. After five minutes, 100 wt % chloroform was fed at a rate of 5.30 g/min and 100 wt % chlorine gas was sparged into the solution at a rate of 3.42 g/min for 90 minutes. Chlorine was fed at 112% of what was required stoichiometrically for the reaction. Samples were taken every 30 minutes. The conversion of chloroform was 98.90% and the selectivity of chloroform to carbon tetrachloride was 99.94%, with the balance of the reacted chloroform producing hexachloroethane.

Example 7

The reactor was charged with 953 grams of a mixture containing 1.02% chloroform in carbon tetrachloride. The reaction temperature was maintained at 35° C. The UV lamp was turned on. After five minutes, 100 wt % chloroform was fed at a rate of 5.78 g/min and 100 wt % chlorine gas was sparged into the solution at a rate of 3.42 g/min for 90 minutes. Chlorine was fed at 100% of what was required stoichiometrically for the reaction of the chloroform being fed. Samples were taken every 30 minutes. The conversion of chloroform was 97.79% and the selectivity of chloroform to carbon tetrachloride was 99.84%, with the balance of the reacted chloroform producing hexachloroethane.

Example 8

The reactor was charged with 1044 grams of a mixture containing 8.93% chloroform in carbon tetrachloride. The reaction temperature was maintained at 35° C. The UV lamp was turned on. After five minutes, 100 wt % chloroform was fed at a rate of 5.76 g/min and 100 wt % chlorine gas was sparged into the solution at a rate of 3.42 g/min for 90 minutes. Chlorine was fed at 100% of what was required stoichiometrically for the reaction of the chloroform being fed. Samples were taken every 30 minutes. The conversion of chloroform was 90.99% and the selectivity of chloroform to carbon tetrachloride was 99.67%, with the balance of the reacted chloroform producing hexachloroethane.

Example 9

In this example the borosilicate glass filter was removed from the lamp. The reactor was charged with 963 grams of a mixture containing 1.24% chloroform in carbon tetrachloride. The reaction temperature was maintained at 35° C. The UV lamp was turned on. After five minutes, 100 wt % chloroform was fed at a rate of 5.78 g/min and 100 wt % chlorine gas was sparged into the solution at a rate of 3.42 g/min for 90 minutes. Chlorine was fed at 100% of what was required stoichiometrically for the reaction of the chloroform being fed. Samples were taken every 30 minutes. The conversion of chloroform was 98.33% and the selectivity of chloroform to carbon tetrachloride was 99.60%, with the balance of the reacted chloroform producing hexachloroethane.

TABLE 2

| Example | 6 | 7 | 8 | 9 |
|---|---|---|---|---|
| lb/hr $CHCl_3$/1000 lbs $CCl_4$ | 321 | 612 | 704 | 613 |
| Feed Mole Ratio ($Cl_2$:$CHCl_3$) | 1.09 | 1.00 | 1.00 | 1.00 |
| Initial $CHCl_3$ in Reactor (wt %) | 0.00% | 1.02% | 8.93% | 1.24% |
| Temperature, ° C. | 35 | 35 | 35 | 35 |
| Borosilicate Glass Filter on Lamp | Yes | Yes | Yes | No |
| $CHCl_3$ Conversion | 98.90% | 97.79% | 90.99% | 98.33% |
| Selectivity to $CCl_4$ | 99.94% | 99.84% | 99.67% | 99.60% |

The data in Table 2 shows that Examples 7, 8, and 9 fall outside practice of the present invention since the selectivity of the reaction to carbon tetrachloride was outside of acceptable ranges. For example, in Example 7, by achieving only 99.84% selectivity, the resultant product stream includes over 1500 ppm hexachloroethane, which is an unacceptable level for most synthetic processes that use carbon tetrachloride for a feedstock. Further distillation of the product stream would therefore be required to remove the hexachloroethane. It is believed that Examples 7, 8, and 9 failed due to the presence of excess chloroform during the reaction.

Various modifications and alterations that do not depart from the scope and spirit of this invention will become apparent to those skilled in the art. This invention is not to be duly limited to the illustrative embodiments set forth herein.

What is claimed is:

1. A method of producing carbon tetrachloride, the method comprising steps of
   (i) providing a carbon tetrachloride feed stream, wherein the carbon tetrachloride feed stream includes from about 99.9 to about 100 wt % of carbon tetrachloride;
   (ii) providing a chlorine gas feed stream;
   (iii) admixing the carbon tetrachloride feed stream and the chlorine gas feed stream to form a first mixture;
   (iv) subjecting the first mixture to electromagnetic radiation to form a free radical mixture including chlorine free radicals;
   (v) providing, after the step (iv) of subjecting, a chloroform feed stream;
   (vi) admixing the chloroform feed stream and the free radical mixture as a reaction mixture to thereby form a product carbon tetrachloride stream; and
   (vii) collecting the product carbon tetrachloride stream without a distillation process.

2. The method of claim 1, wherein the concentration of the chloroform in the reaction mixture is less than 4,000 ppm by weight relative to the weight of the reaction mixture.

3. The method of claim 1, wherein the electromagnetic radiation has a wavelength distribution, based upon relative intensity, where from about 50% to about 60% of the relative intensity has a wavelength of about 280 nm to about 435 nm.

4. The method of claim 1, wherein the electromagnetic radiation has a wavelength distribution, based upon relative intensity, where from about 40% to about 50% of the relative intensity has a wavelength of about 300 nm to about 380 nm.

5. The method of claim 1, wherein the step of admixing the chloroform feed stream and the free radical mixture occurs within a reactor maintained at a temperature of from about 10° C. to about 70° C. and at a pressure of from about 0.9 atmospheres to about 10 atmospheres.

6. The method of claim 1, wherein the product carbon tetrachloride stream includes less than 1,000 ppm by weight hexachloroethane.

7. A method of producing carbon tetrachloride, the method comprising steps of
   (i) providing a carbon tetrachloride feed stream including carbon tetrachloride;
   (ii) providing a chlorine feed stream including chlorine;
   (iii) providing a chloroform feed stream including chloroform;
   (iv) admixing the carbon tetrachloride feed stream, the chlorine feed stream, and the chloroform feed stream to form a reaction mixture, wherein the concentration of chloroform within the reaction mixture is less than 5,000 ppm by weight based upon a total weight of the reaction mixture;
   (v) subjecting the reaction mixture to electromagnetic radiation to form chlorine free radicals; and
   (vi) collecting a product carbon tetrachloride stream from the reaction mixture,
wherein the method achieves a reaction yield relative to chloroform of greater than 99.50%, and a conversion of chloroform to carbon tetrachloride of about 100%.

8. The method of claim 7, wherein the product carbon tetrachloride stream includes less than 500 ppm by weight hexachloroethane.

9. The method of claim 7, wherein the electromagnetic radiation has a wavelength distribution, based upon relative intensity, where from about 50% to about 60% of the relative intensity has a wavelength of about 280 nm to about 435 nm.

10. The method of claim 7, wherein the electromagnetic radiation has a wavelength distribution, based upon relative intensity, where from about 40% to about 50% of the relative intensity has a wavelength of about 300 nm to about 380 nm.

11. The method of claim 7, wherein the product carbon tetrachloride stream includes less than 4,000 ppm by weight chloroform.

12. The method of claim 7, wherein the product carbon tetrachloride stream is subjected to additional electromagnetic radiation in a polishing UV reactor.

13. A method of producing carbon tetrachloride, the method comprising steps of
(i) admixing a carbon tetrachloride feed stream, a chlorine gas feed stream including free radicals, and a chloroform feed stream, to thereby react chloroform with the free radicals to form carbon tetrachloride as a product, wherein the carbon tetrachloride feed stream includes from about 99.9 to about 100 wt. % of carbon tetrachloride;
(ii) allowing the reaction of the chloroform with the free radicals to achieve a reaction yield relative to chloroform of greater than 99.00%; and
(iii) collecting a product carbon tetrachloride stream that includes less than 2,500 ppm by weight hexachloroethane without a distillation process.

14. The method of claim 13, wherein the method achieves a reaction yield relative to chloroform of greater than 99.50%.

15. The method of claim 13, wherein the method achieves a reaction yield relative to chloroform of greater than 99.99%.

16. The method of claim 13, wherein the product carbon tetrachloride stream includes less than 1,000 ppm by weight hexachloroethane.

17. The method of claim 13, wherein the product carbon tetrachloride stream includes less than 500 ppm by weight hexachloroethane.

18. The method of claim 13, wherein the product carbon tetrachloride stream includes less than 4,000 ppm by weight chloroform.

19. The method of claim 13, wherein the product carbon tetrachloride stream includes less than 1,000 ppm by weight chloroform.

* * * * *